US007202222B2

(12) United States Patent
Ramazanov et al.

(10) Patent No.: US 7,202,222 B2
(45) Date of Patent: Apr. 10, 2007

(54) METHODS FOR TREATMENT OF OBESITY AND EFFECTIVE FAT LOSS PROMOTION

(75) Inventors: Arthur Ramazanov, Warwick, NY (US); Zakir Ramazanov, Warwick, NY (US)

(73) Assignee: National Bioscience Corporation, Chester, NY (US)

( * ) Notice: Subject to any disclaimer, the term of this patent is extended or adjusted under 35 U.S.C. 154(b) by 249 days.

(21) Appl. No.: 10/660,256

(22) Filed: Sep. 11, 2003

(65) Prior Publication Data

US 2004/0147460 A1 Jul. 29, 2004

Related U.S. Application Data

(60) Provisional application No. 60/438,113, filed on Jan. 6, 2003.

(51) Int. Cl.
*A61K 31/7024* (2006.01)
*A61K 31/704* (2006.01)
*A61K 31/353* (2006.01)

(52) U.S. Cl. .......................... 514/33; 514/456
(58) Field of Classification Search ............... None
See application file for complete search history.

(56) References Cited

U.S. PATENT DOCUMENTS

| 4,451,465 | A | 5/1984 | White et al. |
| 4,772,631 | A | 9/1988 | Holloway et al. |
| 4,977,148 | A | 12/1990 | Holloway et al. |
| 4,999,377 | A | 3/1991 | Caulkett et al. |
| 5,626,849 | A | 5/1997 | Hastings et al. |
| 5,783,603 | A | 7/1998 | Majeed et al. |
| 5,804,596 | A | 9/1998 | Majeed et al. |
| 6,340,482 | B1 | 1/2002 | Jones |
| 6,827,950 | B2 | 12/2004 | Hong et al. |

FOREIGN PATENT DOCUMENTS

JP 2002-187845 7/2002

OTHER PUBLICATIONS

Babenkova et al., Vestnik oftalmologii, (Jul.-Aug. 1999) vol. 115, No. 4, pp. 22-24.*
Brasaemle et al., (1997) "Post-translational Regulation of Perillipin Expression", *The Journal of Biological Chemistry*, 272:9378-9387.
Brasaemle et al. (2000) "Perilipin A Increases Triacylglycerol Storage by Decreasing the Rate of Triacylglycerol Hydrolysis", *The Journal of Biological Chemistry*, 275:38486-38493.
Chaudhry and Granneman (1999) "Differential regulation of functional responses by β-adrenergic receptor subtypes in brown adipocytes", *Am. J. Physiol.*, 277:R147-R153.
Clifford et al., (1998) "Dephosphorylation of perilipin by protein phosphatases present in rat adipocytes", *FEBS Letters*, 435:125-129.

Clifford et al., (2000) "Translocation of Hormone-sensitive Lipase and Perilipin upon Lipolytic Stimulation of Rat Adipocytes", *The Journal of Biological Chemistry*, 275:5011-5015.
Geodakyan et al., (1992) "High-performance liquid chromatographic method for determination of mangiferin, likviritin and dihydroquercetin in rat plasma and urine", *J. of Chromatography*, 577:371-375.
Greenberg et al. (1991) "Perilipin, a Major Hormonally Regulated Adipocyte-specific Phosphoprotein Associated with the Periphery of Lipid Storage Droplets", *The Journal of Biological Chemistry*, 266:11341-11346.
Greenberg et al., (1993) "Isolation of cDNAs for perilipins A and B: Sequence and expression of lipid droplet-associated proteins of adipocytes", *Proc. Natl. Acad. Sci. USA*, 90:12035-12039.
Han et al., (1998) "Norepinephrine-Augmenting Lipolytic Effectors from *Asitlbe thunbergii* Rhizomes", *J. Nat. Prod.*, 61:1006-1011.
Haraguchi et al., (1996) "Inhibition of aldose reductase by dihydrofavonols in *Engelhardtia chrysolepis* and effects on other enzymes", *Experientia*, 52: 564-567.
Haraguchi et al., (1996) "Protection against Oxidative Damage by Dihydroflavonols in *Engelhardtia chrysolepis*", *Biosci. Biotech. Biochem.* 60:945-948.
Heymsfield et al., (1998) "*Garcinia cambogia* (Hydroxycitric Acid) as a Potential Antiobesity Agent: A Randomized Controlled Trial", *JAMA*, 280:1596-1600.
Holm et al., (2000) "Molecular Mechanisms Regulating Hormone-Sensitive Lipase and Liposlysis", *Annu. Rev. Nutr.*, 20:365-393.
Igarashi et al., (1996) "Effect of Astilbin in Tea Processed from Leaves of *Engelhardtia chrysolepis* on the Serum and Live Lipid Concentrations and on the Erythrocyte and Liver Antioxidative Enzyme Activities of Rats", *Biosci. Biotech. Biochem.*, 60:513-515.
Kellner-Weibel et al., (2001) "Evidence that newly synthesized esterified cholesterol is deposited in existing cytoplasmic lipid inclusions", *Journal of Lipid Research*, 42:768-777.
Leonhardt et al., (2002) "Hydroxycitrate Has Long-Term Effects on Feeding Behavior, Body Weight Regain and Metabolism after Body Weight Loss in Male Rats", *J. Nutr.*, 132:1977-1982.
Londos et al., (1995) "Perilipin: unique proteins associated with intracellular neutral lipid droplets in adipocytes and steroidogenic cells", *Biochem. Society Transactions*, 23:611-615.
Martinez-Botas et al., (2000) "Absence of perilipin results in leanness and reverses obesity in Lepr$^{db/db}$ mice", *Nature Genetics*, 26:474-479.
Mauriege et al., (1999) "Regional and gender variations in adipose tissue lipolysis in response to weight loss", *J. of Lipid Research*, 40:1559-1571.
Miyase et al., (1996) "Araliasaponins XII-XVIII, triterpene saponins from the roots of Aralia chinensis", *Phytochemistry* 42:1123-1130.

(Continued)

*Primary Examiner*—Phyllis G. Spivack
(74) *Attorney, Agent, or Firm*—Darby & Darby (57) ABSTRACT

Methods for treating obesity, reducing total weight and reducing body fat mass by administering a composition comprising dihydroquercetins and root-derived aralosides A, B, C and D is disclosed.

6 Claims, 3 Drawing Sheets

OTHER PUBLICATIONS

Miyase et al., (1996) "Araliasaponins I-Xi, triterpene saponins from the roots of Aralia decaisneana", *Phytochemistry*, 41:1411-1418.

Morimoto et al., (1997) "Norepinephrine-induced Lipolysis in Rat Fat Cells from Visceral and Subcutaneous Sites: Role of Hormone-sensitive Lipase and Lipid Droplets", *J. of Lipid Research*, 38:132-138.

Morimoto et al., (2000) "Mechanism of the stimulatory action of okadaic acid on lipolysis in rat fat cells", *J. of Lipid Research*, 41:199-204.

Morimoto et al., (2000) "Substrate-Dependent Lipolysis Induced by Isoproterenol", *Biochem and Biophys Res Comm*, 274:631-634.

Morimoto et al., (2001) "Relationships between lipolysis induced by various lipolytic agents and hormone-sensitive lipase in rat fat cells", *J. of Lipid Research*, 42:120-127.

Muls et al., (2001) "The effects of orlistat on weight and on serum lipids in obese patients with hypercholesterolemia: a randomized, double-blind, placebo-controlled, multicentre study", *International Journal of Obesity*, 25:1713-1721.

Murphy et al., (2000) "New insights into the mechanisms of lipid-body biogenesis in plants and other organisms", *Biochemical Society Transactions*, 28:710-711.

Osterlund T. (2001) "Structure-function relationships of hormone-sensitive lipase", *Eur. J. Biochem.*, 268:1899-1907.

Sakai et al., (1994) "Oleanolic acid saponins from root bark of Aralia elata", *Phytochemistry*, 35:1319-1324.

Satoh et al., (1994) "Oleanolic acid saponins from root-bark of Aralia elata", *Phytochemistry*, 36:147-152.

Sedykh et al., (1986) "The Influence of the Aralia Mandshurica Tincture, Aminalon of Their Combination for Memorization of Texts", *New Medicinal Preparation from Plants of Siberia and the Far East*, p. 132.

Servetnick et al., (1995) "Perilipins Are Associated with Cholesteryl Ester Droplets in Seroidogenic Adrenal Cortical and Leydig Cells", *The Journal of Biological Chem*, 270:16970-16973.

Snow J.M. (1995) "*Coleus forskohlii* Willd. (Lamiaceae)", *The Protocol Journal of Botanical Medicine*, pp. 39-42.

Souquet et al., (2000) "Phenolic Composition of Grape Stems", *J. Agric. Food Chem.*, 48:1076-1080.

Souza et al., (1998) "Overexpression of Perilipin A and B Blocks the Ability of Tumor Necrosis Factor α to Increase Lipolysis in 3T3-L1 Adipocytes", *The Journal of Biological Chemistry*, 273:24665-24669.

Tansey et al., (2001) "Perilipin ablation results in a lean mouse with aberrant adipocyte lipolysis, enhanced leptin production, and resistance to diet-induced obesity", *PNAS*, 98:6494-6499.

Theriault et al., (2000) "Modulation of hepatic lipoprotein synthesis and secretion by taxifolin, a plant flavonoid", *Journal of Lipid Research*, 41:1969-1979.

Tiukavkina et al., (1997) "Dihydroquercetin—a new antioxidant and biologically active food additive", *Vopr Pitan*, 6:12-15.

Wang et al., (1994) "Chemical analysis of main medicinal species of genus Aralia", *CHung Kuo Chung Yao Tsa Chih*, 19:6-8.

Yamamoto et al., (2000) "Anti-obesity effects of lipase inhibitor CT-11, an extract from edible herbs, Nomame Herba, on rats fed a high-fat diet", *International Journal of Obesity*, 24:758-764.

Yoshikawa et al., (1995) "Medicinal foodstuffs. I. Hypoglycemic constituents from a garnish foodstuff "taranome," the young shoot of *Aralia* elata SEEM: elatosides G, H, I, J. and K", *Chem Pharm Bull*, 43:1878-1882.

Yoshikawa et al., (1996) "Bioactive saponins and Glycosides. VI. Elatosides A and B, Potent Inhibitors of Ethanol Absorption, from the Bark of *Aralia elata* SEEM. (Araliaceae): The Structure-Requirement in Oleanolic Acid Glucuronide-Saponins for the Inhibitory Activity", *Chem. Pharm. Bull.*, 44:1915-1922.

Yoshikawa et al., (1996) "Bioactive saponins and glycosides. VII. On the hypoglycemic principles from the root cortex of *Aralia* elata Seem.: Structure related hypoglycemic activity of oleanolic acid oligoglycoside", *Chem Pharm Bull*, 44:1923-1927.

Yu et al., (1994) "Triterpenoid saponins from the roots of *Aralia spinifolia*", *J Nat Prod*, 57:978-982.

Zeng et al., (1994) "Chemical constituents of *Aralia* decaisneana Hance", *Chung Kuo Chung Yao Tsa Chih*, 19:550-551.

Zweytick et al., (2000) "Intracellular lipid particles of eukaryotic cells", *Biochemica et Biophysica Acta*, 1469:101-120.

Okuyama, et al., "Analgesic Principles from Aralia cordata Thunb.", Chemical & Pharmaceutical Bulletin, vol. 39, No. 2, Feb. 1991, pp. 405-407.

Patent Abstract, Method of Producing Antiobesity Drug From Buds of a Plant (Aralia Elata), Patent No. JP2002187845, Published Jul. 5, 2000.

Aleshkina, Y. A. (1962). Pharmacological Properties of *Aralia Mandshurica* Institute of Medicinal Plants, Russian Academy of Science. Medicinal Plants of Russia, Moscow, Russia pp. 258-264.

Arimura N, et al. (2004). The peroxisome proliferator-activated receptor gamma regulates expression of the perilipin gene in adipocytes. Biol Chem.12; 279(11):10070-10076.

Brasaemle DL, et al. (2004). Proteomic Analysis of Proteins Associated with Lipid Droplets of Basal and Lipolytically Stimulated 3T3-L1 Adipocytes J. Biol. Chem., vol. 279, Issue 45, 46835-46842.

Chen TH, et al., (2001). The in vitro inhibitory effect of flavonoid astilbin on 3-hydroxy-3-methylglutaryl coenzyme A reductase on Vero cells. Zhonghua Yi Xue Za Zhi (Taipei). 64(7):382-387.

Chung CK, Jung ME. (2003). Ethanol fraction of *Aralia elata* Seemann enhances antioxidant activity and lowers serum lipids in rats when administered with benzo(a)pyrene. Biol Pharm Bull. 26(10): 1502-1504.

Dzhumaeva Tl. Radivoz MI, Konakova EN. (1980). Androgenic effect of *Aralia mandshurica* extract. Pharmacy in Russian Far East, pp. 92-95.

Dyakov DI. (1971). On the Influence of *Aralia mandshurica* on the Pulse Arterial Pressure during Prescribed Physical Workloads. Biologically Active Substances from Flora and Fauna of the Far East and Pacific Ocean. Vladivostok, 117-118.

Garcia A., et al. (2004) The amino and carboxyl termini of perilipin a facilitate the storage of triacylglycerols. J Biol Chem. 279(9):8409-8416.

Gubehenko PP, Fruentov NK (1982). A comparative study of effectiveness of adaptogenic plants *Aralia mandshurica, Eleutherococcus* and other plants adaptogens as agents for enhancing the working capacity of the flying personnel. Khabarovsk State Medical Institute, Khabarovsk, USSR.

Gubina G.P. (1962). Clinical Applications of *Aralia mandshurica* Tincture. In Medicinal Phytopreparations from plants, Moscow, Russia 263-269.

Ivanov IS, Savkina GD, S.Ya. Sokolov Sya (1971). Treatment of Periodontitis with Saparal. Central Scientific Research Institute of Stomatology, Moscow. In: Biologically active substances in the flora and fauna of the Soviet Far East and Pacific Ocean. Vladivostok; Russia, 1971, pp. 122-123.

Kazakevich VV (1971). The Effect of *Aralia Mandshurica* extract on Physical Work Capacity of Animals and Humans. Medical Institute, Khabarovsk. In: Biologically active compounds in flora and fauna of Soviet Far East. pp. 119-120.

Kazakevich VV. (1972). On the Influence of *Aralial mandshurica* tincture on the Central Nervous System: In Medicinal Remedies of the Far East. Vladivostok: Far East Scientific Center of the Academy of Science of the USSR, 186-189.

Kem PA, et al. (2004). Perilipin Expression in Human Adipose Tissue Is Elevated with Obesity The Journal of Clinical Endocrinology & Metabolism vol. 89, No. 3 1352-1358.

Kim JS, Shim SH, Chae S, Han SJ, Kang SS, Son KH, Chang HW, Kim HP, Bae K (2005) Saponins and other constituents from the leaves of Aralial elata. Chem Pharm Bull (Tokyo). 53(6): 696-700.

Komissarenko BT (1962). Aralia—A New Stimulating and Tonic Agent. *Soviet Medicine* (*Sovetskaya meditisina*): 95, No. 3; pp. 115-117.

Kryukovskaya, E.V., Kudrin A.N (1991), Effect of Aralia mandshurica extract on Adaptive mechanisms and Tolerance of Central Nervous system under Ischemic condition. I.M. Sechenov First Moscow Medical Institute. Pharmacology and Toxicology, pp. 47-50.

Lee EB, Kim OJ, Kang SS, Jeong C. (2005) Araloside A, an anti-ulcer constitutent from the root bark of Aralia elata. Biol Pharm Bull. 28(3): 523-6.

Levin RM, Leggett RE, Whitbeck C, Murakami T, Kambara T, Aikawa K (2004) Oral Kohki Tea and its protective effect against in vitro ischemic damage to the bladder. Neurourol Urodvn. 23 (4): 355-360.

Levin RM, Kawashima Y, Leggett RE, Whitbeck C, Horan P, Mizutani K. (2002) Effect of oral Kohki tea on bladder dysfunction induced by severe partial outlet obstruction. J Urol. 167(5): 2260-2266.

Levin RM, Leggett RE, Whitbeck C, Matsumoto S., Ohto N., Ikeda T., Mizutani K (2006) Kohki Tea protects rabbit bladder from Ischemia/ Reperfusion-Induced Contractile dysfunction. Neurourol Urodyn. In Press.

Plotnikov MB, Plotnikov DM, et al. (2004). Hemorheological and antioxidant effects of Ascovertin in patients with sclerosis of cerebral arteries. Clin Hemorheol Microcirc. 30(3-4): 449-52.

Russian Pharmacopoeia, 1982. USSR Ministry of Health Administration for Introduction of New Therapeutic Agents and Medical Technology Pharmacopoeia Committee. Moscow-1982.

Sim Joon-Soo, *Hai* Lin Zhao, *Da* Wei Li, et al., (2005) Effects of Saponins from the Root Bark of *Aralia elata* on the Transport of Chondroitin Sulfate in Caco-2 Cell Monolayers and Rats *Biol. Pharm. Bull.* 28(6) 1043-1048.

Sokolov SYa, Monogarov VD, Sobolev VL, et al. (1971). The Effect of Aralial Mandshurica Saponins On Recovery Processes in Sportsman Following Heavy Physical Loads. "Biologically active substances in the flora and fauna of the Soviet Far East and Pacific Ocean," Vladivostok; 1971, pp. 113-114.

Sokolov SYa (1971). The Dependence Between Chemical Structure and Neurotropic Action of Glycosides of Oleonolic Acid. In: Biologically active substances in the flora and fauna of the Soviet Far East and Pacific Ocean. Vladivostok; 1971, pp. 40-41.

Sokolov S. Ya, Ostrovsky NN, Maksimova RG, et al. (1971). Experimental Pharmacological and Clinical Study of the Tonicizing Properties Of Aralosides from *Aralia Mandshurica*. All-Union Institue of Medicinal Piants, Moscow. Biologically active substances in the flora and fauna of the Soviet Far East and Pacific Ocean. Vladivostok; 1971, pp. 41-42.

Sokolov S Ya. (1982). Pharmacological Properties of Aralia Mandshurica Saponins. Russian Academy of Science. In: *Medicinal Agents from Plants;* Editor: Prof. A.D. Turova. Moscow, State Publishing Press for Medicinal Sciences, pp. 270-277.

Tomatsu M, Ohnsihi-Kameyama M, Shibamoto N. (2003). Aralin, a new cytotoxic protein from Aralia elata, inducing apoptosis in human cancer cells. Cancer Lett. 199 (1): 19-25.

Turova AD (1974). Aralia mandshurica (Thom tree) Rupr. At Maxim. In: Medicinal Plants of USSR and their application. Moscow, Medicine Press. Ed. AD Turova, pp. 21-26.

Yan R, Xu Q (2001) Astilbin selectively facilitates the apoptosis of interleukin-2-dependent phytohemagglutinin-activated Jurkat cells. Pharmacol Res. 44 (2):135-139.

Yatsino Al, Seyfulla Khl, Turova AD (1971) Neurotropic Properties of Tinctures of Aralia Mandshurica and Schmidt's Aralia In a Comparative Study. Biologically active substances in the flora and faun of the Soviet Far East and Pacific Ocean. Vladivostok; pp. 42-44.

Yoshikawa M., Yamahara J (1996). Inhibitory effect of oleanene-type triterpene oligoglycosides on ethanol absorption: the structure -activity relationships. IN: Saponins Used in Traditional and Modern Medicine. Ed. By Walter & Yamasaki, Plenum Press, New York, pp. 207-217.

Xu Q, Wu F, Cao J, Chen T, Jiang J, Saiki I, Koda A. (1999). Astilbin selectively induces dysfunction of liver-infiltrating cells—novel protection from liver damage. Eur J Pharmacol. 14; 377(1):93-100.

Wang Y., et al. (2003). Perilipin Expression in Human Adipose Tissues: Effects of Severe Obesity, Gender, and Depot Obes Res. 11(8):930-936.

Zhang HH., et al. (2003). Lipase-selective Functional Domains of Perilipin A Differentially Regulate Constitutive and Protein Kinase A-stimulated Lipolysis J. Biol. Chem., vol. 278, Issue 51, 51535-51542.

* cited by examiner

METHODS FOR TREATMENT OF OBESITY AND EFFECTIVE FAT LOSS PROMOTION

This application claims priority to provisional U.S. application No. 60/438,113 filed Jan. 6, 2003 under 35 U.S.C. § 119(e), which is incorporated by reference.

Numerous references, including patents, patent applications, and various publications are cited and discussed in the description of this invention. The citation and/or discussion of such references is provided merely to clarify the description of the present invention and is not an admission that any such reference is "prior art" to the present invention. All references cited and discussed in this specification are incorporated herein by reference in their entirety and to the same extent as if each reference was individually incorporated by reference.

FIELD OF THE INVENTION

The present invention encompasses pharmaceutical compositions for the treatment of obesity. These compositions comprise dihydroquercetins (dihydroquercetin 3-rhamnoside and its aglycon dihydroquercetin) and the triterpene saponins known as aralosides or elatosides. The compositions of the present invention effectively promote total weight loss and body fat mass loss. Therefore, the present invention is also directed to methods for treating obesity, reducing total weight, and reducing body fat mass by administering the compositions of the invention. The invention also embraces methods for disrupting the perilipin shell of lipid droplets and stimulating the activity of hormone-sensitive lipase.

BACKGROUND OF THE INVENTION

Obesity among adults and children has become increasingly prevalent in almost all industrialized countries. According to the National Institute of Health, over the past two decades the incidence of obesity has increased more than 50 percent. The primary causes of obesity are not precisely understood, although social, dietary, and genetic factors are thought to be involved. Obesity represents a major risk factor for cardiovascular diseases, diabetes, osteoporosis, and atherosclerosis. It is believed that a 10% reduction of weight corresponds to a 20% reduction in coronary disease incidence, whereas a 10% increase in weight is associated with a 30% increase in coronary disease incidence ["Obesity: Preventing and Managing the Global Epidemic" in *WHO Obesity Technical Report Series* 894. World Health Organization, Switzerland, 2000; Rose. Nutr Metab Cardiovasc Dis 1991 1:37–40; Ashley and Kannel. J. Chronic Dis. 1974 27:103–114]. Thus, reduction of obesity is of major importance to improve general health.

The term "obesity" refers to a state of excess body fat mass. This body fat mass is comprised of adipocytes. The primary function of adipocytes is to store excess energy in the form of triacylglycerol, and to release this stored energy as free fatty acid in times of increased energy need. Triacylglycerol is stored within adipocytes in the form of lipid droplets. The lipid droplets are composed of a hydrophobic core of neutral lipids (such as triacylglycerol) surrounded by a phospholipids monolayer, in which protein is embedded. Upon increased demand for energy (e.g., during fasting or exercise), this stored triacylglycerol is hydrolyzed to yield glycerol and free fatty acids. These hydrolysis products are release into the blood stream. The free fatty acids are then taken up by, and used for the generation of ATP in, a wide variety of tissues.

The balance of energy storage versus release by adipocytes is tightly regulated. For example, the anti-lipolytic hormone insulin stimulates the assembly of triacylglycerol lipid droplets in adipocytes. Conversely, lipolytic hormones, such as epinephrine, norepinephrine, catecholamines, and Tumor Necrosis Factor alpha (TNFα), activate the hydrolysis of triglycerides. Reduction of the body fat mass occurs when pro-lipolytic effects predominate, such that triacylglycerol stores are hydrolyzed and adipocyte mass decreases.

Two key players in the regulation of the adipocyte lipolytic pathway are Hormone Sensitive Lipase (HSL) and perilipin.

The HSL enzyme catalyzes the rate limiting step of triglycerides hydrolysis. Lipolytic hormones activate HSL by stimulating its enzymatic activity and/or promoting its translocation from the cytoplasm to the periphery of the lipid droplet. This activation is thought to be mediated, at least in part, by phosphorylation of HSL by cAMP-dependent protein kinase (PKC).

Perilipin is the most abundant protein of the adipocyte lipid droplet. Up to four different isoforms of the perilipin protein may be generated by alternate splicing of a transcript produced from a single perilipin gene (Servetnick, et al. J. Biol. Chem. 1995 270:16970–16973). Perilipin protein is located at the periphery of the lipid droplet (Greenberg, et al. J. Biol. Chem. 1991 266:11341–11346), where it is thought to act as a barrier that precludes access of HSL to the stored triglycerides (Clifford, et al. FEBS Letters 1998 435:125–129; Souza, et al. J. Biol. Chem. 1998 273:24665–24669; and Brasaemle, et al. J. Biol. Chem. 2000 275:38486–38493). Lipolytic hormones antagonize the barrier function of perilipin, thereby allowing HSL to hydrolyze the lipid droplet triglycerides (Clifford, et al. J. Biol. Chem. 2000 275:5011–5015). This antagonism may be mediated, in part, by phosphorylation of perilipin by cAMP-dependent protein kinase (PKC).

The link between perilipin and HSL, and the importance of perilipin in the regulation of triglycerides storage, has been shown by a number of studies. Ectopic expression of perilipin in fibroblastic 3T3-L1 pre-adipocyte cells in vitro caused the formation of intracellular lipid droplets (Brasaemle, et al. J. Biol. Chem. 2000 275:38486–38493). These cells stored significantly more triacylglycerol that control cells. This increased storage was due to decreased hydrolysis of triacylglycerol. Ectopic expression of perilipin in 3T3-L1 cells also blocked the ability of TNFα to stimulate lipolysis (Souza, et al. J. Biol. Chem. 1998 273:24665–24669).

Mice lacking the perilipin gene are more muscular, have less fat, are resistant to diet-induced obesity, and have higher energy expenditure (Martinez-Botas, et al. Nature Genetics 2000 26:474–479; Tansey, et al. Proc Natl Acad Sci USA. 2001 98:6494–6499). In these mice, lipid droplet triglycerides are broken down as soon as they are made. These effects are related to the constitutive activation of HSL observed in these mice (Martinez-Botas, et al. Nature Genetics 2000 26:474–479). This result in mice establishes that disruption of perilipin function results in a decrease in fat mass, and prevents obesity.

Therefore, HSL and perilipin are attractive targets for drugs to treat obesity. Treatments which can activate HSL activity and simultaneously disrupt the perilipin shell of lipid droplets will promote body fat mass loss by stimulating lipolysis. The discovery of a novel pharmaceutical composition which has these effects, thus represents a significant advance in the treatment of obesity.

A number of dietary supplements and pharmaceuticals have been introduced for the promotion of fat loss (see, for example, U.S. Pat. Nos. 5,626,849; 5,804,596; 5,783,603; and 6,340,482). Most of the currently available pharmaceuticals for weight loss work by suppressing appetite via central mechanisms (Stunkard. Life Sci. 1982 30:2043–2055; Weiser, et al. J Clin Pharmacol. 1997 37:453–473). See, for example U.S. Pat. No. 5,783,603, which concerns the use of potassium hydroxy-citric acid to suppress appetite and reduce fatty acid synthesis.

Certain compounds have been disclosed that are able to induce weight loss by mechanisms other than appetite suppression (e.g., through stimulation of the peripheral metabolic rate of adipose tissue). For example, U.S. Pat. Nos. 4,451,465; 4,772,631; 4,977,148; and 4,999,377 disclose compounds possessing thermogenic properties which cause few or no deleterious side effects (such as cardiac stimulation) at the suggested dose. Another compound, Orlistat, blocks absorption of ingested fat by inhibiting pancreatic lipase.

The most commonly used natural supplements for promotion of fat loss include hydroxycitric acid (U.S. Pat. No. 5,626,849), L-carnitine, ma huang (ephedrine) and green tea, forskolin, and citrus extract (U.S. Pat. No. 6,340,482). In addition, chromium picolinate is sold as an ingredient in "fat burner" formulas (Evans. Int J Biosocial Med Res. 1989 11:163–80). However, subsequent clinical studies have failed to demonstrate any significant effect of chromium picolinate, hydroxycitric acid, forskolin or other natural dietary supplements on body fat mass reduction (Hasten, et al. Int J Sport Nutr 1992 2:343–50; Clancy, et al. Int J Sport Nutr. 1994 4:142–53). A well-controlled study found no difference in the magnitude of body fat mass or lean body mass between those who took the above mentioned dietary formulas and those who took placebo (Trent and Thieding-Cancel. J Sports Med Physical Fitness 1995 35:273–80).

The ineffectiveness of prior described dietary formulas in the treatment of obesity and promotion of fat mass reduction may be related to the fact that none simultaneously disrupts the perilipin shell of lipid droplets and stimulates HSL activity.

The essential ingredients of the novel composition have been used individually for treatment of prevention of various health disorders, and thus have a long history of safe use in humans. However, neither of these components has been used for the treatment of obesity and promotion of fat loss in mammals, and in particular in humans.

Figure 1:
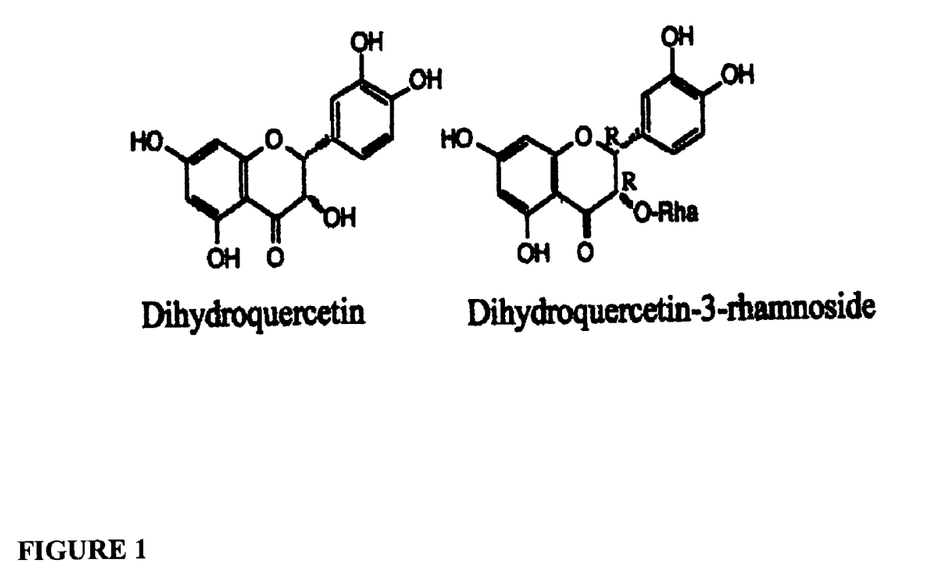
FIG. 1 depicts the structural formulas of aglycon dihydroquercetin (chemical name: 3, 3', 4', 5, 7-pentahydroxyflavone) and dihydroquercetin-3-rhamnoside (chemical name: 3, 3', 4', 5, 7-pentahydroxyflavone-3-rhamnoside). "Rha" is the rhamnoside sugar moiety.

Dihydroquercetin-3-rhamnoside and aglycon dihydroquercetin (see FIG. 1) are flavonoids found commonly in many different plant species, such as Grape stem (*Vitis vinifera*) and the leaves of *Rhododendron caucasicum* and *Larix siberica*. The dihydroquercetins in *Engelhardtia chrysolepis* tea, known as kohki tea, have been consumed in Vietnam, Japan and other Asian cultures for centuries (Kasai, et al. Chem. Pharm. Bull. 1988 36:4167–4170; Igarashi, et al. Biosci. Biotec. Biochem. 1996 60:513–515; Mizutani, et al. Nippon Shokuhin Shinsozai Kenkyukaishi. 1998 1:51–64). Dihydroquercetins possess superior antioxidant activity to suppress lipid peroxidation and protect against the destructive affects of free radicals (Haraguchi, et al. Biosci Biotechnol Biochem 1996 60:45–48). Dihydroquercetins also stabilize blood vessels and protect against factors that cause atherosclerosis and cardiac, hepatic, and bronchiopulmonary diseases. In addition, dihydroquercetins possess anti-allergy and anti-inflammatory activity (Tiukavkina, et al. Nutrition, Moscow 1997 6:12–15; Teselkin, et al. Biofizika. 1996 41:620–624; Tiukavkina, et al. Nutrition 1996 2:33–38), and protect the liver from toxins (Xu, et al. Eur J Pharmacol 1999 377:93–100). Dihydroquercetins have been approved in Russia as a medical preparations for use in antioxidant and capillary protective preparations (Russian National Pharmacopoeia Article 42-2398-94, approved on Jul. 29, 1996).

Dihydroquercetins are known to inhibit HMG-CoA reductase, a key enzyme in cholesterol synthesis (Chen, et al. Zhonghua Yi Xue Za Zhi, Taipei 2001 64:382–387) and lower plasma triglycerides levels (Igarashi, et al. Biosci. Biotec. Biochem. 1996 60:513–515; Mizutani, et al. Nippon Shokuhin Shinsozai Kenkyukaishi 1998 1:51–64). However, these effects of dihydroquercetins have not been associated with promotion of weight loss or fat reduction. This lack of functional association is consistent with the activity of other compounds used for the treatment of hypercholesteremia (e.g., statins), which reduce cholesterol and/or triglycerides levels without promoting fat loss. Thus, dihydroquercetins in isolation are not sufficient to effectively treat obesity and promote weight loss.

Figure 2:
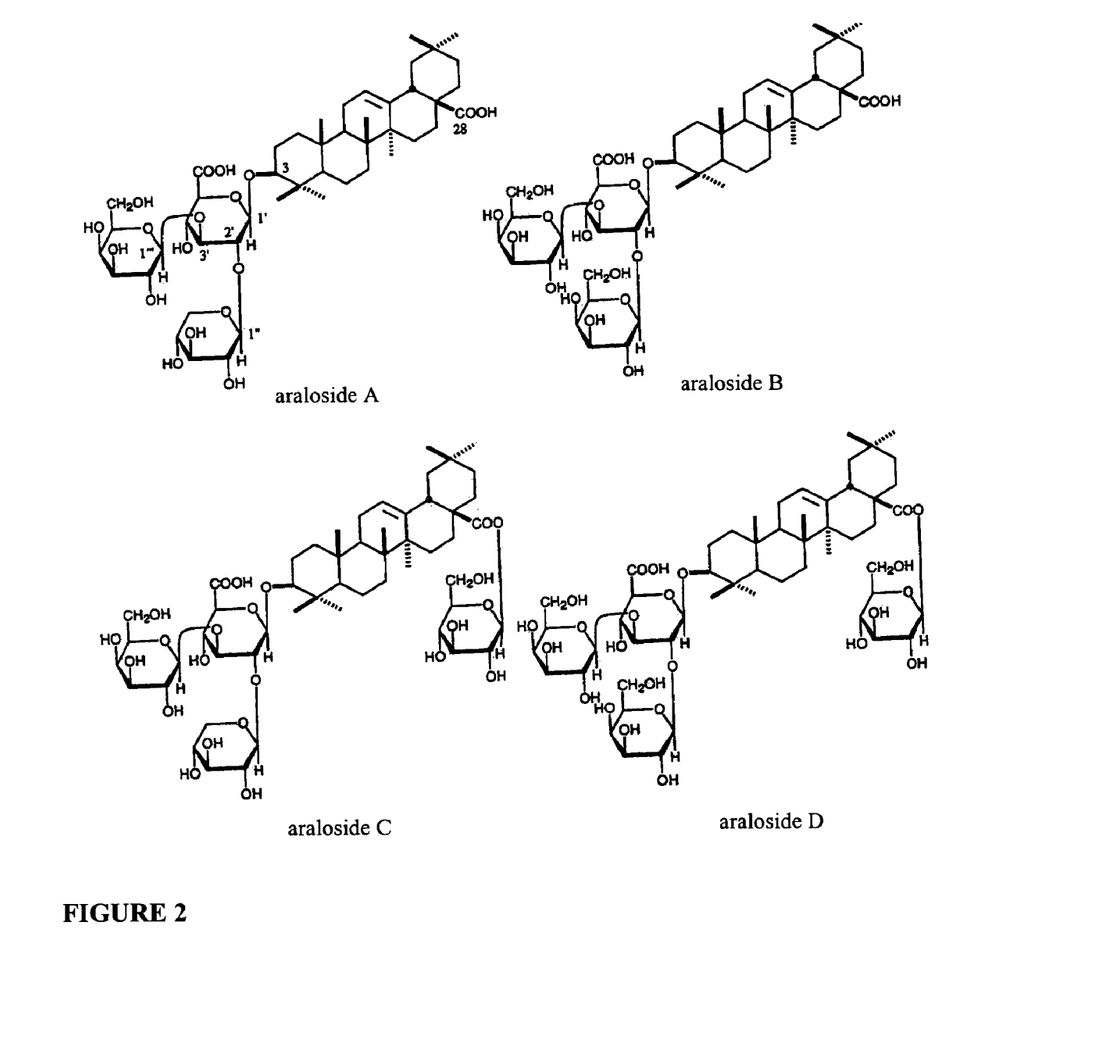
FIG. 2 depicts the structural formulas of aralosides A, B, C, and D.

Plants of the genus *Aralia* are a natural source of the triterpene saponins known collectively as aralosides or elatosides. The terms "aralosides" and "elatosides" are derived from the scientific names of the *Aralia* plants from which these triterpene saponins may be derived (e.g., *Aralia elata*). These aralosides (or elatosides) have been shown to constitute the active ingredients of medicinal *Aralia* preparations. Eleven major triterpene saponins designated as aralosides A, B, C, D, E, F, G, H, I, J, and K have been isolated from *Aralia* (Yoshokawa, et al Chem. Pharm. Bull. 1994 43:1878–1882). The major active triterpene saponins of medical *Aralia* preparations are aralosides A, B, C, and D (see FIG. 2).

Based on various clinical studies, *Aralia* tincture has been included in the Russian State Pharmacopoeia XI under the name "Saporali" (Sokolov. Pharmacology and Chemistry, Moscow Science Publishing, Russia, 1968). Aralosides stimulate the central nervous and immune systems, possess anti-stress properties, and protect against unfavorable environmental conditions such as hypoxia or viral infections. Aralosides also improve long term memory (Sedykh, et al. "The Influence of the *Aralia mandshurica* tincture, animalon or their combination for memorization of texts," New Medicinal Preparations from Plants of Siberia and Far East. Tomsk State University, Russia: 1986. p. 132). Furthermore, aralosides reduce ethanol absorption (Yoshikawa, et al. Chem Pharm Bull. Tokyo 1993 41:2069–2071; Yoshikawa, et al. Chem Pharm Bull. Tokyo 1996 44:1915–1922); possess analgesic properties (Okuyama, et al. Chem Pharm Bull. Tokyo 1991 39:405–407); and reduce blood sugar levels (Yoshikawa, et al. Chem Pharm Bull. Tokyo 1996 44:1923–1927).

It has now been discovered that a combination of dihydroquercetins and aralosides is effective for treating obesity.

SUMMARY OF THE INVENTION

The present invention encompasses a pharmaceutical composition for the treatment of obesity comprised of dihydroquercetins and aralosides. Preferably, the composition of the invention comprises about 4–99% by weight of dihydroquercetins and about 1–80% by weight of aralosides. More preferably, the composition of the invention comprises about 15–25% by weight of dihydroquercetins and about 15–25%% by weight of aralosides. Most preferably, the composition of the invention comprises about 15–17% by weight of dihydroquercetins and about 15–17% by weight of aralosides.

The present invention also provides a method for treating obesity in mammalian subjects in need of such treatment, which method comprises administering an effective amount of dihydroquercetins and aralosides. Preferably, this method is performed where the total daily dose of dihydroquercetins is about 150 to 225 mg, and the total daily dose of aralosides is about 150 to 225 mg. More preferably, this method is performed where the total daily dose of dihydroquercetins is about 150 mg and the total daily dose of aralosides is about 150 mg.

Accordingly, the present invention also relates to methods for reducing total body weight, and for reducing body fat mass, in mammalian subjects in need thereof, which method comprises administering an effective amount of dihydroquercetins and aralosides. The present invention also provides methods for disrupting the perilipin shell of lipid droplets, and for stimulating the activity of hormone sensitive lipase, in obese mammalians subject, which method comprises administering an effective amount of dihydroquercetins and aralosides.

DETAILED DESCRIPTION OF THE INVENTION

Definitions

As used herein, the term "dihydroquercetins" encompasses dihydroquercetin 3-rhamnoside and its aglycon dihydroquercetin. The chemical name for aglycon dihydroquercetin is 3, 3', 4', 5, 7-pentahydroxyflavone. The chemical name for dihydroquercetin-3-rhamnoside is 3, 3', 4', 5, 7-pentahydroxyflavone-3-rhamnoside.

As used herein, the term "aralosides" encompasses triterpene saponins found naturally in plants of the genus *Aralia*, including the eleven major triterpene saponins designated as aralosides A, B, C, D, E, F, G, H, I, J, and K. Preferably the aralosides include aralosides A, B, C, and D.

As used herein, the term "total body weight" refers to the total mass of a subject, generally measured in kilograms, where total body weight is the sum of body fat mass and non-fat body mass. As used herein, the term "body fat mass" refers to the total mass of adipocyte tissue in a subject. The amount of body fat mass is generally expressed in kilograms, and represents the portion of a subject's total body weight due to adipocytes. As used herein, the term "non-fat body mass" or "lean body mass" refers to total mass of non-adipocyte tissue in a subject. The amount of non-fat body mass is generally expressed in kilograms, and represents the portion of a subject's total body weight due to tissue types other than adipocytes, such as muscle.

As used herein, the term "lipid droplets" refers to the natural bodies for triacylglycerol storage comprising a hydrophobic core of neutral lipids (such as triacylglycerol), a surrounding phospholipids monolayer, and the proteins (such as perilipin) embedded in the phospholipids monolayer. As used herein, the term "adipocyte lipid droplets" refers to the lipid droplets of adipocytes; and the term "serum lipid droplets" refers to the lipid droplets present in the blood stream. These serum lipid droplets may be isolated from the plasma portion of a blood sample.

As used herein, the term "perilipin shell" refers to the network of perilipin protein found at the periphery of lipid droplets.

As used herein, the term "serum triglycerides" refers to the total amount of triglycerides present in whole blood.

The Novel Compositions

The compositions of the present invention for use in treating obesity and promoting weight loss comprise dihydroquercetins and aralosides, which may be derived from any source, including natural and synthetic sources. The compositions of the present invention comprise from about 4% to 99% by weight of dihydroquercetins and from about 1 to 80% by weight of aralosides. More preferably, the compositions of the present invention comprise from about 15% to 25% by weight of dihydroquercetins and from about 15% to 25% by weight of aralosides. Most preferably, the compositions of the present invention comprise from about 15 to 17% by weight of dihydroquercetins and from about 15% to 17% by weight of aralosides.

The compositions of the present invention may include additional ingredients known for use in promoting weight loss and in treating obesity those used in other weight-loss promoting formulations; including, for example, Siberian *Rhodiola rosea* and *Rhaponticum carthamoides* root extract, L-carnitine, green tea, citrus extract, and chromium picolinate.

The compositions for oral administration in accordance with the present invention may be formulated, in solid or liquid phase, in a conventional manner using one or more physiologically acceptable carriers or excipients. For example, the compositions may take the form of tablets or capsules prepared by conventional means with pharmaceutically acceptable excipients such as binding agents (e.g., pregelatinized maize starch, polyvinylpyrrolidone, or hydroxypropyl methylcellulose); fillers (e.g., lactose, microcrystalline cellulose, or calcium hydrogen phosphate); lubricants (e.g., magnesium stearate, talc, or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, flavoring, coloring, and sweetening agents as appropriate. The preparations may be suitably formulated to give controlled release of the active compounds.

Producing the Novel Composition

In one embodiment, the compositions may be produced using commercially available preparations of dihydroquercetins and aralosides. For example, pure aglycon dihydroquercetin (~99% pure) is available from Indofine Chemicals (Somerville, N.J., USA). A pure 1:1 mixture of dihydroquercetin 3-rhamnoside and aglycon dihydroquercetin (~99% pure) is available from the Georgian Academy of Science, Tbilisi, (Republic of Georgia). A purified aralosides mixture (~99% pure) of aralosides A, B, C, and D is available from the Russian Institute of Natural Products, VILAR (Moscow).

In another embodiment, the dihydroquercetins and aralosides may be chemically synthesized. For example, dihydroquercetin-3-rhamnoside may be synthesized as described in Ohmori, et al. Tetrahedron Lett. (2000) 41:5537–5541.

Using such commercially available and/or chemically synthesized preparations, the composition of the invention may be made by combining about 4% to 99% by weight of dihydroquercetins; about 1 to 80% by weight of aralosides; and about 0–95% by weight of a pharmaceutically acceptable carrier or excipient. More preferably, the composition is produced using these commercially available preparations by combining about 15–25% by weight of dihydroquercetins; about 15–25% by weight of aralosides; and about 50–70% by weight of a pharmaceutically acceptable carrier or excipient. Most preferably, the composition is produced using these commercially available preparations by combining about 15–17% by weight of dihydroquercetins; about 15–17% by weight of aralosides; and about 66–70% by weight of a pharmaceutically acceptable carrier or excipient.

In a preferred embodiment, the dihydroquercetins and aralosides are isolated from their natural sources, which include plants. Preferred natural sources of dihydroquercetins are the leaves of *Engelhardtia chrysolepsis*, *Rhododendron caucasicum*, or stem of *Vitis vinifera*. Preferred natural sources of aralosides are the bark and root of plants of the genus *Aralia*: a preferred *Aralia* species is *Aralia mandshurica* (also know as *Aralia elata*). A preferred method of isolation is solvent-based extraction. The components may be independently extracted from their natural sources, and these independent extracts combined. Preferably, the components are simultaneously extracted from their combined natural sources.

For example, the components may be simultaneously extracted from their combined natural sources to produce a dried powdered extract that comprises about 4% to 99% by weight of dihydroquercetins; about 1 to 80% by weight of aralosides; and about 0–95% by weight of other extracted plant materials. More preferably, the components are simultaneously extracted from their combined natural sources to produce a dried powdered extract that comprises about 15–25% by weight of dihydroquercetins; about 15–25% by weight of aralosides; and about 50–70% by weight of other extracted plant materials. Most preferably, the components are simultaneously extracted from their combined natural sources to produce a dried powdered extract that comprises about 15–17% by weight of dihydroquercetins; about 15–17% by weight of aralosides; and about 66–70% by weight of other extracted plant materials. These dried powdered extracts may be used "as is", without the addition of any carriers or excipients.

Prior to extraction, the natural source plant materials are preferably processed so as to reduce the surface area to volume ratio of the materials. Such processing may include cutting, grinding, and milling of the materials. Preferably, the plant materials are also dried prior to extraction. Most preferably the materials are dried to a moisture content of 8–15%. The materials may be dried by exposure to air, preferably under elevated temperature so as to facilitate evaporation of moisture from the plant materials. Drying is preferably performed at a temperature of from 20–70° C., most preferably from at a temperature of from 40–60° C.

Preferred solvents for extraction include water, a low molecular weight alcohol (molecular weight ≦about 70), or combinations of these. The solvent, for example, may comprise at about 70 percent by volume of water and at about 30 percent by volume of a low molecular weight alcohol. Low molecular weight alcohols that may be used for extraction include ethanol, methanol, propanol, and iso-propanol. The preferred low molecular weight alcohol is ethanol. Preferably, the low molecular weight alcohol comprises at least about 70 percent by volume of the solvent, with water comprising the balance of the solvent.

Solvent-based extraction comprises contacting the solvent and natural sources for several hours, preferably under agitation and at elevated temperature. Most preferably, the solvent and natural sources (e.g., plant materials prepared as described above) are contacted under agitation for about 4–6 hours, at a temperature of about 35° C. to about 70° C. Following extraction the remaining natural source solids are removed from the extract, for example by filtration or decanting. Preferably, the removed solids are subjected to a second round of solvent-based extraction, under similar conditions. In this case, the extracts from the first and second extractions are then combined. Following extraction using a solvent containing alcohol, the alcohol may be evaporated from the extract, preferably under reduced pressure and at elevated temperature. Most preferably the temperature is between 60 and 70° C.

Preferably, these alcohol-free extracts are then dried to solid form. A preferred method of drying uses a spray drier, such as the Spray Drier model VRA-1 (Manufactured by Vzduchotechnika, Novo Mesto, Slovakia). Most preferably, the extract is spray dried using 180° C. input temperature and 85° C. output temperature. Spray drying yields a dry powdered form of the extract.

The concentration of dihydroquercetin and aralosides in a sample of dried powdered extract may be determined by chromatography. The preferred chromatographic technique is High Pressure Liquid Chromatography (HPLC). Protocols for HPLC are well described in the art (see, for example, "Current Protocols in Molecular Biology." Ausubel, et al. eds. John Wiley & Sons: 1994). A preferred HPLC technique for quantification of aralosides in a sample is described in Xu, et al. Yao Xue Xue Bao (1998) 33:933–936.

Use of the Composition to Treat Obesity

The pharmaceutical compositions of the invention may be administered orally to obese mammalian subjects. The compositions of the invention that are effective in treating obesity and promoting weight loss comprise from about 4% to 99% by weight of dihydroquercetins and from about 1 to 80% by weight of aralosides. A preferred composition comprises from about 15% to 25% by weight of dihydroquercetins and from about 15% to 25% by weight of aralosides. Most preferably, the composition comprises from about 15–17% by weight of dihydroquercetins and about 15–17% by weight of aralosides.

A preferred dosing regimen for the treatment of obesity provides a total daily dose of about 150 to 225 mg dihydroquercetins and about 150 to 225 mg aralosides. A more preferred dosing regimen provides total daily doses of about 150 mg dihydroquercetins and about 150 mg aralosides.

In the methods of the invention, the compositions of the invention may be employed alone, or in combination with other ingredients or formulations, such as other weight-loss promoting ingredients or formulations. These other weight loss promoting ingredients of formulations may include, for example, *Rhodiola rosea* and *Rhaponticum carthamoides* root extract, Magnolia bark extract, L-carnitine, green tea, citrus extract, or chromium picolinate The effectiveness of the compositions of the invention for treating obesity may be assessed by various techniques. These techniques may involve standard techniques well established in the art, including immunoassays (such as immunoblotting and immunohistochemistry), antibody production, chromatography, and gel electrophoresis (see, for example, "Molecular Cloning: A Laboratory Manual." $3^{rd}$ Edition. Sambrook, et al. CSH Laboratories Press: 2001; "Using Antibodies: A Laboratory Manual." Harlow and Lane. CSH Laboratories Press: 1999; and "Current Protocols in Molecular Biology." Ausubel, et al. eds. John Wiley & Sons: 1994).

A. Total Weight and Body Fat Mass

Total body weight may be determined, for example, with a standard beam scale. Percent body fat may estimated, for example, from body density derived from underwater weighing. This percent may be used to calculate body fat mass. Fat-free body mass may be calculated by subtracting body fat mass from total body weight. Effective body fat mass loss and total weight loss may be quantitated by comparing measurements for each obtained prior to onset of treatment with those obtained during and/or after onset of treatment. An effective treatment for obesity will reduce total body weight and body fat mass.

B. Disruption of the Perilipin Shell of Lipid Droplets

Levels of perilipin protein on adipocyte lipid droplets or serum lipid droplets may be measured. Preferably, perilipin levels are quantitated following immunodetection of perilipin protein. Quantitation may be based, for example, on radiometric, colorimetric, or fluorescence assays. For example, the perilipin shell of lipid droplets may be visualized, and perilipin protein content of lipid droplets quantitated, as described in Greenberg, et al. J. Biol. Chem. 1991 266:11341–11346; Morimoto, et al. Biochem. Biophys. Res. Comm. 2000 274:631–634; or Souza, et al. J. Biol Chem. 1998 273:24665–24669.

C. Hormone Sensitive Lipase Activity

The levels of HSL activity may be measured either indirectly or directly. Indirect assays measure the release of free fatty acids and/or glycerol, where the level of free fatty acid and glycerol release is proportional to the activity of the HSL enzyme. These assays are based upon the established requirement for HSL to catalyze the breakdown of stored triglycerides into glycerol and free fatty acids. In one indirect assay, the levels of free fatty acids in the blood are quantitated (see, for example, Example 2 below). In an alternate assay, the release of free fatty acids from isolated visceral or subcutaneous adipocytes may be measured (see, for example, Morimoto, et al. J. Lipid Res. 1997 38:132–138; Morimoto, et al. J. Lipid Res. 2000 41:199–204). In yet another alternate protocol, the release of glycerol from isolated adipocytes may be measured (see, for example, Clifford, et al. FEBS Letters 435:125–129; Souza, et al. J. Biol. Chem. 1998 273:24665–24669; Morimoto, et al. J. Lipid Res. 2000 41:199–204).

Direct assays measure the activity of HSL to catalyze the hydrolysis of a supplied substrate. For example, the HSL activity in a crude adipocyte lysate may be measured using the radiolabelled substrates triolein (Morimoto, et al. J. Lipid Res. 1997 38:132–138); trioleoyglycerol (Morimoto, et al. J. Lipid Res. 2000 41:199–204); or cholesteryloleate (Morimoto, et al. J. Lipid Res. 2001 42:120–127). In an alternate protocol, the HSL is first partially purified from adipocyte lysate (Morimoto, et al. J. Lipid Res. 1997 38:132–138).

EXAMPLES

The present invention is next described by means of the following examples. However, the use of these and other examples anywhere in the specification is illustrative only, and in no way limits the scope and meaning of the invention or of any exemplified form. Likewise, the invention is not limited to any particular preferred embodiments described herein. Indeed, many modifications and variations of the invention may be apparent to those skilled in the art upon reading this specification, and can be made without departing from its spirit and scope. The invention is therefore to be limited only by the terms of the appended claims, along with the full scope of equivalents to which the claims are entitled.

In accordance with the present invention there may be employed conventional molecular biology, microbiology, protein expression and purification, antibody, and recombinant DNA techniques within the skill of the art. Such techniques are explained fully in the literature. See, e.g., *DNA Cloning: A Practical Approach*, Volumes I and II (Glover ed.: 1985); *Oligonucleotide Synthesis* (Gait ed.: 1984); *Nucleic Acid Hybridization* (Hames & Higgins eds.: 1985); *Transcription And Translation* (Hames & Higgins, eds.:1984); *Animal Cell Culture* (Freshney, ed.:1986); *Immobilized Cells And Enzymes* (IRL Press: 1986); Perbal, *A Practical Guide To Molecular Cloning* (1984); Ausubel et al., eds. *Current Protocols in Molecular Biology*, (John Wiley & Sons, Inc.:1994); Sambrook et al. *Molecular Cloning: A Laboratory Manual*, Third Edition (Cold Spring Harbor Laboratory Press: 2001); Harlow and Lane. *Using Antibodies: A Laboratory Manual* (Cold Spring Harbor Laboratory Press: 1999); *PCR Primer: A Laboratory Manual, Second Edition*. Dieffenbach and Dveksler, eds. (Cold Spring Harbor Laboratory Press: 2003); and Hockfield et al. *Selected Methods for Antibody and Nucleic Acid Probes* (Cold Spring Harbor Laboratory Press: 1993).

Example 1

Manufacture of the Novel Composition

Extraction of the Dihydroguercetins and Aralosides Composition

For dihydroquercetins, the leaves of *Engelhardtia chrysolepsis* were harvested in the middle of summer in the South Vietnam and dried under continuous warm air flow at a temperature of 45–50° C. for about 17 hours to a moisture content of about 8–15%. The dried material was then milled to a particle size of about 10 mm.

For aralosides, *Aralia mandshurica* bark and root was harvested in early August in the Russian Far East, cleaned of soil debris, sliced into chips about 20 mm thick, and dried in a drying chamber under warm (about 60° C.) air-flow for about 2.5 days, until the moisture content was reduced to about 8–15%.

One thousand kilograms each of prepared *Engelhardtia chrysolepsis* and *Aralia manchurica* plant materials were placed together into a 4000 liter extraction vessel with 2000 liters of solvent. The solvent was a 70%:30% (volume/volume) mixture of ethanol and water.

The plant materials and solvent were contacted, under agitation, for about 5 hours, at a temperature of about 60° C. Following this initial extraction, the remaining plant materials were removed by filtration through a 40 mesh sieve. The filtered plant materials were subjected to a second round of extraction with an additional 1000 liters of solvent. The plant materials and solvent were agitated together in an extraction vessel for about 5 hours, at a temperature of about 60° C. Following this secondary extraction, the remaining plant materials were removed by filtration through a 40 mesh sieve and discarded.

The initial and secondary extracts were combined, and the alcohol evaporated under reduced pressure (about 250 bars) and elevated temperature (about 60–70° C.). This alcohol-free solution was spray dried using a Spray Drier model VRA-1 (Vzduchotechnika, Novo Mesto, Slovakia), at an input temperature of 180° C. and an output temperature of 85° C. The resultant dry powdered extract was subjected to High performance Liquid Chromatography analysis to determine the concentrations of dihydroquercetin and aralosides.

Analysis of Dihydroquercetins

The concentration of dihydroquercetins in the dried powdered extract was determined via HPLC, using a Water Alliance 2690 High Performance Liquid Chromatography (HPLC) apparatus equipped with a 996 photodiode array detector (Waters, Milford, Mass., USA). The HPLC column was a reversed-phase $C_{18}$ Symmetry column (3.9 mm×150 mm) with 5 µm packing (Axis HPLC Column, MicroSolv Technology Corp., N.J. Cat. # 59150-21). The mobile phase solvents consisted of methanol (Phase A) and 0.4% phosphoric acid in water (Phase B). The flow rate was adjusted to 1.8 ml/minutes, and the detection wavelengths were 290 nm and 365 nm.

An HPLC reference standard 1:1 mixture of dihydroquercetin 3-rhamnoside and aglycon dihydroquercetin (~99% pure) was purchased from Georgian Academy of Science, Tbilisi, (Republic of Georgia). A stock solutions of this standard was prepared in methanol to a concentration of approximately 1 mg/ml. This stock solution was diluted in methanol to obtain at least three reference standard solutions of varying concentration. 0.5 ml aliquots of these prepared samples were filtered through a 0.22 µm membrane filter. Then 20 µl of filtered sample was injected into the HPLC column. HPLC results, from triplicate injections of these standard solutions starting with the most diluted, were used to generate a calibration curve (standard concentration versus detector response, as peak area).

For the experimental sample, 500 mg of dried powdered extract was placed into a 25 ml volumetric flask. This extract was dissolved in 15 ml methanol under agitation. A 0.5 ml aliquot of dissolved extract was filtered through a 0.22 µm membrane filter. Then 20 µl of filtered sample was injected into the HPLC column. The HPLC values for the experimental sample were interpolated in the calibration curve to determine the concentration of dihydroquercetins in the sample. The results are expressed as percentage of the component in the material analyzed (w/w), taking into account the dilutions made and the initial sample weighted.

The exact concentration of dihydroquercetins in the dried powdered extract varies slightly from preparation to preparation. Generally, this method provides for a dried powdered extract comprising about 15–25% by weight of dihydroquercetins. For example, in one preparation the combined concentration of dihydroquercetin 3-rhamnoside and its aglycon dihydroquercetin in the dried powdered extract was about 20.4% by weight.

Analysis of Aralosides

The total concentration of aralosides in the above described extract was determined using the HPLC method described by Xu, et al. Yao Xue Xue Bao (1998) 33:933–936. HPLC analysis was performed on a Waters Alliance 2690 HPLC system, equipped with a 906 photodiode array detector (Waters, Milford, Mass., USA). The analytical column was a Supelco SIL-LC-18 column (Sigma Aldrich Corp, St Louis, USA). The mobile phase consisted of methanol, 1% HOAc, and tetrahydrofuran (500:110:1), at pH 3.4. The flow rate was set to 1.2 ml/minutes, and the detection wavelength was 205 nm.

An HPLC reference standard mixture of aralosides A, B, C, and D (~99% pure) was purchased from the Russian Institute of Natural Products (Moscow). Stock solutions of this standard were prepared in methanol to a concentration of approximately 1 mg/ml. The stock solution was diluted in methanol to obtain at least three reference standard solutions of varying concentration. 0.5 ml aliquots of these prepared samples were filtered through a 0.22 µm membrane filter. Then 20 µl of filtered sample was injected into the HPLC column. HPLC results, from triplicate injections of these standard solutions starting with the most diluted, were used to generate a calibration curve (standard concentration versus detector response, as peak area).

For the experimental sample, 400 mg of dried powdered extract was placed in a 25 ml volumetric flask a dissolved in 20 ml methanol under agitation. The HPLC values for experimental samples were interpolated in the calibration curve to determine the concentration or aralosides in the sample. The results are expressed as percentage of the component in the material analyzed (w/w), taking into account the dilutions made and the initial sample weighted.

The exact concentration of aralosides in the dried powdered extract will vary slightly from preparation to preparation. Generally, this method provides for a dried powdered extract comprising about 15–25% by weight of aralosides. For example, in one preparation the concentration of total aralosides in the dried powdered extract was about 19.8% by weight.

The Dried Powdered Extract as a Composition for Treating Obesity

The dried powdered extract (prepared as described above) generally comprises about 15–25% by weight of dihydroquercetins and about 15–25% by weight of aralosides. This dried powdered extract is used "as is" to make gelatin capsules for oral administration. Each single dose capsule contains a 300 mg dose of the dried powdered extract. Thus, a single 300 mg dose contains about 50–75 mg of dihydroquercetins; about 50–75 mg aralosides; and about 150–200 mg of other solvent-extracted plant materials.

Example 2

Use of Novel Composition to Treat Human Subjects

Clinical Trial Design

Thirty-two (n=32) obese volunteers (body mass index >25.2 and <33.4) took part in a 15-week clinical trial. Selection criteria were the absence of clinically manifested diabetes and a waist/hip circumference ratio (WHR)>1.0. All subjects were apparently healthy and reported moderate alcohol consumption. The subjects were informed of the trial design both orally and in writing, and informed consent for participation was obtained. For thirty days prior to the 15-week clinical trial, patients underwent a period of diet counseling and surveillance (see Table 1). At the onset of the study period (baseline), there were no significant differences in physical characteristics or nutrient intake between subjects of the Dried Powdered Extract and Placebo groups (see Table 1).

TABLE 1

Average baseline physical characteristics and nutrient intake

| Variable assessed | Placebo group (n = 16) | Dried Powdered Extract group (n = 16) |
|---|---|---|
| Physical characteristics | | |
| Age (years) | 43 ± 12 | 42 ± 10 |
| Height (cm) | 172 ± 17 | 170 ± 15 |
| Total body weight (kg) | 94.2 ± 5.8 | 94.4 ± 5.0 |
| Body fat mass (kg) | 33.6 ± 2.1 | 33.3 ± 2.2 |
| Daily nutrient intake | | |
| Total calories intake | 1700 ± 150 | 1700 ± 160 |
| Carbohydrates (%)* | 50.0 ± 1.6 | 51.3 ± 3.2 |
| Fat (%)* | 23.3 ± 4.2 | 24.8 ± 1.8 |
| Protein (%)* | 18.1 ± 2.3 | 18.2 ± 3.6 |

*As percent of total energy intake.

TABLE 2

Results of clinical treatment studies

| | Baseline | | After clinical trial | |
|---|---|---|---|---|
| Variable | Dried Powdered Extract (n = 16) | Placebo (n = 16) | Dried Powdered Extract (n = 13) | Placebo (n = 14) |
| Total weight (kg) | 94.4 ± 5.0 | 94.2 ± 5.8 | 90.1 ± 2.2 (−4.3 kg)‡ | 93.7 ± 3.0 (−0.5 kg) |
| Body fat mass (kg) | 33.3 ± 2.2 | 33.6 ± 2.1 | 29.2 ± 1.2 (−4.1 kg) | 32.9 ± 1.4 (−0.7 kg) |
| Fat-free body mass (kg) | 61.1 ± 2.1 | 60.6 ± 1.8 | 60.9 ± 1.3 (−0.2 kg) | 60.8 ± 0.6 (−0.2 kg) |
| SLD perilipin (arbitrary units) | 60.7 ± 10.6 | 60.2 ± 12.5 | 44.3 ± 14.5 | 58.1 ± 11.2 |
| Serum triglycerides (mmol/L) | 3.6 ± 0.2 | 3.5 ± 0.5 | 1.8 ± 0.7 (−49%) | 3.4 ± 0.8 (−03%) |
| Plasma free fatty acids (μmol/L) | 730 ± 40 | 740 ± 30 | 870 ± 50 (+16%) | 755 ± 45 (+02%) |
| Adipocyte HSL activity (mUnits/mg total protein) | 5.2 ± 1.1 | 5.1 ± 0.9 | 8.1 ± 1.4 (+35%) | 5.2 ± 1.2 (+02%) |

‡Change from baseline.
SLD = Serum lipid droplets.

During the 15-week clinical trial, subjects were randomly assigned to receive 300 mg of the dried powdered extract (n=16) or 300 mg placebo (n=16), to be taken three times a day before meals. Based on this dosing regimen, total daily doses were about 150 to 225 mg dihydroquercetins and about 150 to 225 mg aralosides. During the clinical phase subjects were required to come to the Medical Center twice a week for a session during which they were weighed and asked about compliance. Food record analyses and symptom questionnaire responses were also collected at these sessions. Thirteen subjects (n=13) of the Dried Powdered Extract group, and fourteen subjects (n=14) of the Placebo group completed the 15-week clinical trial.

On admission (baseline) and at the conclusion of the 15 week clinical trial, patients were evaluated for body fat mass index, serum lipid droplets perilipin levels, serum triglycerides levels, plasma free fatty acids levels, and adipocyte hormone sensitive lipase (HSL) activity (see Table 2).

Determination of Body Fat Mass

Total body weight was measured in kilograms (kg) with a standard beam scale. The percentage of body fat was then estimated from body density derived from underwater weighing. This percentage was used to calculate body fat mass (in kg). Fat-free body mass, or lean body mass, was calculated by subtracting body fat mass from total body weight.

Baseline total weight, body fat mass, and fat-free body mass values for the Dried Powdered Extract and Placebo groups were not significantly different (see Table 2). By the end of the 15-week clinical trial, the Dried Powdered Extract group subjects showed a significant decrease in total weight and body fat mass, while no significant changes were observed in the Placebo group. Note that weight loss of the Dried Powdered Extract group was predominantly due to loss of body fat mass: fat-free mass values for the Dried Powdered Extract group after clinical trial were not significantly different from baseline. These results show that the dried powdered extract comprising dihydroquercetins and aralosides is effective to reduce body fat mass and total weight in obese subjects.

Isolation of Serum Lipid Droplets

Venous blood samples were collected at baseline and after 15 weeks of clinical trial. Five ml of blood plasma was centrifuged at 1,000 rpm for 10 minutes. Next, 1 ml cold phosphate buffer containing 1 mM dithiothreitol, 10 µg/ml leupeptin (Roche Diagnostics Corporation, Indianapolis) was added to obtained supernatant. Three ml of supernatant+ buffer was layered onto a continuous 0.2–2.2 molar sucrose gradient. Ultra-centrifugation was performed at 40,000 rpm for 3 hours at 4° C. in a Beckman L8-80MR Ultra Centrifuge with type 65 rotor (Beckman, Fullerton, Calif.), and 1 ml gradient fractions were gently collected from the top to the bottom using a 5 ml syringe. Each 1 ml fraction was examined under microscopy using an Axioskop 2 Model Microscope with a mounted Axicam Hi-Resolution digital camera model DSC-S75 (Carl Zeiss, N.Y.). Photomicrographs were taken using an 100× objective lens. The serum lipid droplets were contained in the 1 ml fraction removed from the top of the sucrose gradient.

Levels of Serum Lipid Droplets Perilipin

Levels of perilipin on the isolated serum lipid droplets were quantitated using Western blot immunoanalysis. Sodium dodecyl sulfate-polyacrylamide gel electrophoresis (SDS-PAGE) of lipid droplets was performed using a 10 to 20% acrylamide gradient gel (Laemmli. Nature 1970 227: 680–685).

Samples for electrophoresis contained a 0.5 ml aliquot of a serum lipid droplets sucrose gradient fraction in a buffer of 80 mM Tris-HCl (pH 6.8); 0.1M dithiothreitol, 70 mM SDS, and 1.0 mM glycerol, final concentration. These samples were boiled for 1 minute at 100° C., then centrifuged at 12,000×g for 1 min. The supernatant of each sample was removed, and the protein concentration therein determined by measuring absorbance at 280 nm (where 1 absorbance unit=50 µg protein). Supernatant aliquots containing 100 µg of protein were separated on 10–20% linear gradient SDS-PAGE gels according to Laemmli (1970). Proteins were electrophoretically transferred onto nitrocellulose membranes using a transfer buffer of 39 mM glycine and 48 mM Tris (pH7.2). After transfer, membranes were placed in a blocking buffer containing 0.5% Tween-20, 0.2% gelatin, and 3.0% dry milk for at least 1 hour at room temperature. Membranes were then incubated with polyclonal anti-perilipin antibody (1:1000 dilution) provided by Dr. Miguel Jimenez del Rio (Technological Institute of Las Palmas, Spain) for 2 hours at room temperature. Subsequently, membranes were incubated with a secondary alkaline phosphatase-conjugated anti-rabbit IgG (Bio-Rad Labs, Calif.) for 1 hour at room temperature. Following each incubation membranes were washed six times for 10 minutes in a buffer of 0.5% Tween-20, 0.2% gelatin, and 0.3% dry milk.

Figure 3:
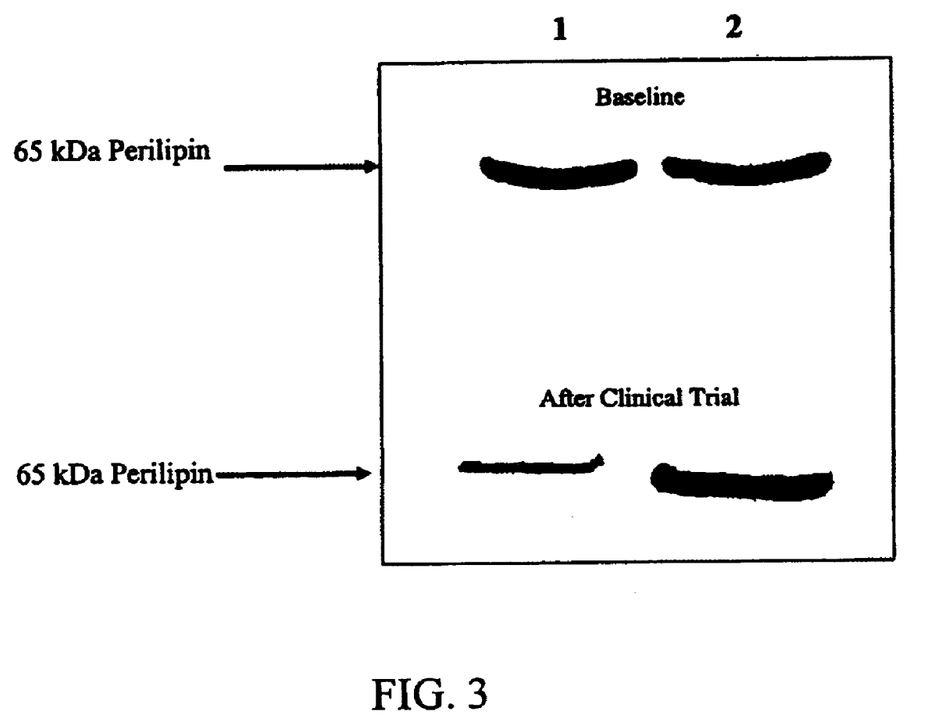
FIG. 3 depicts a Western blot of electrophoresed serum lipid droplets protein probed with an antibody raised against purified human perilipin. Samples were from subjects at Baseline and After Clinical Trial as indicated. Samples in column 1 are from a Dried Powdered Extract group subject. Samples in column 2 are from a Placebo group subject. Each lane contains 100 μg of total serum lipid droplets protein. The size of perilipin, in kilodaltons (kDa), is indicated.

Bound antibody was detected using the alkaline phosphatase substrates nitroblue tetrazolium and bromo-chloroindolyl phosphate (See FIG. 3). The relative concentration of perilipin protein in each sample was determined by scanning densitometry (Hoefer GS-300 Scanning Densitometer, San Francisco, Calif., USA). These scanning densitometry results were converted to arbitrary units for comparison (see Table 2). This densitometric analysis revealed that perilipin protein levels were significantly reduced in subjects of the Dried Powdered Extract group: from 60.7±10.6 arbitrary units at baseline to 44.3±14.5 arbitrary units after the 15-week clinical trial. Conversely, no significant changes in perilipin protein levels were observed for the Placebo group: from 60.2±12.5 at baseline to 58.1±11.2 arbitrary units after the 15-week clinical trial. These results show that the dried powdered extract comprising dihydroquercetins and aralosides is effective to disrupt the perilipin shell of serum lipid droplets, consistent with its ability to promote fat mass loss.

Levels of Serum Triglycerides

Serum triglycerides levels were determined as described in Friedewald, et al. Clin. Chem. 1972 18:499–502. For this assay, blood samples were collected from subjects prior to the onset of treatment and at the end of the 15-week clinical trial (See Table 2).

At baseline, serum triglycerides levels of the Dried Powdered Extract and Placebo groups were not significantly different (See Table 2. After the clinical trial, the Dried Powdered Extract group showed a significant reduction in triglycerides levels, while the Placebo group showed no significant change. These results show that the dried powdered extract comprising dihydroquercetins and aralosides is effective to reduce serum triglycerides levels.

Levels of Plasma Free Fatty Acids (FFA)

The levels of plasma fatty acids from were quantified following methods previously described (Frayn, et al. Clin Chim Acta 1993 216:183–9 and Fredriksson, et al. Methods Enzymol. 1981 71:636–64) using the none esterified fatty acids (NEFA C) kit (Wako Chemicals USA, Inc. Cat. # 994-75409) and a microtiter plate reader (Vectra VL Series 4, Hewlett Packard, Sunnyvale, Calif.).

At baseline, total plasma FFA levels of the Dried Powdered Extract and Placebo groups were not significantly different (See Table 2. After the clinical trial, the Dried Powdered Extract group showed a significant increase in plasma FFA levels, while the Placebo group showed no significant change. These results show that the dried powdered extract comprising dihydroquercetins and aralosides increases plasma FFA levels. This dried powdered extract-induced increase of plasma FFA may reflect alterations in both lipolysis (breakdown of triglycerides) and fatty acid metabolism (assembly to fatty acids into triglycerides).

Adipocyte Hormone Sensitive Lipase activity

Analysis of HSL activity in adipocytes was performed essentially as described in Frayn, et al. Clin. Chim. Acta. (1993) 216:183–189.

One day before beginning the clinical trial, and at the end of the 15-week clinical trial, a subcutaneous fat biopsy was collected from each subject. For biopsy, a small cutaneous incision (1 cm) was made, and approximately 400–500 mg of subcutaneous adipose tissue was surgically removed from the exposed subcutaneous fat deposit. Approximately 100 mg of adipose tissue were homogenized at 4° C. in 0.8 ml buffer (pH 7.4). The buffer contained 0.25 M sucrose, 1 mM EDTA, 1 mM dithiothreitol, and the 20 µg/ml each of the protease inhibitors leupeptin and antipain. Homogenized samples were then centrifuged at 100,000 g for 45 min at 4° C. in a Beckman ultracentrifuge. The fat free supernatant was recovered for analysis of HSL activity, using 1(3)-mono-[3H]oleoyl-2-oleylglycerol as substrate in a reaction for 30 min at 37° C. All samples were incubated in duplicate, and were analyzed on the same occasion. One unit of enzyme activity is defined as 1 µmol of fatty acid released per minute at 37° C. (Mauriege, et al. J. Lipid Res. 1999 40:1559–1571; Fredriksson, et al. Methods Enzymol. 1981 71:636–646).

At baseline, adipocyte HSL activity of the Dried Powdered Extract and Placebo groups were not significantly different (See Table 2). After the clinical trial, the Dried Powdered Extract group showed a significant increase adipocyte HSL activity, while the Placebo group showed no significant change. These results show that the dried powdered extract comprising dihydroquercetins and aralosides increases adipocyte HSL activity, consistent with its ability to increase plasma FFA levels.

DISCUSSION

These clinical results show that the dried powdered extract comprising 15–25% by weight of dihydroquercetins and 15–25% by weight of aralosides is effective to treat obesity. The effective dosing regimen of dried powdered extract provided a total daily dose of about 150–225 mg of dihydroquercetins and about 150–225 mg of aralosides. This composition promotes total weight loss and body fat mass loss. This effect is most likely due to disruption the perilipin shell of serum lipid droplets and simultaneous stimulation of adipocyte HSL activity. Low perilipin levels and high HSL activity stimulate lipolysis, leading to loss of fat mass.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all values are approximate, and are provided for description.

Patents, patent applications, publications, product descriptions, and protocols are cited throughout this application, the disclosures of which are incorporated herein by reference in their entireties for all purposes.

What is claimed is:

1. A method for treating obesity which comprises administering to a mammalian subject in need of such treatment an effective amount for treating obesity of a composition comprising dihydroquercetins and root-derived aralosides A, B, C, and D.

2. The method of claim 1, wherein the total daily dose of dihydroquercetins is about 150 to 225 mg, and the total daily dose of root-derived aralosides A, B, C, and D is about 150 to 225 mg.

3. The method of claim 1, where wherein the total daily dose of dihydroquercetins is about 150 mg and the total daily dose of root-derived aralosides A, B, C, and D is about 150 mg.

4. The method of claim 1 wherein the subject is a human.

5. A method for reducing total body weight which comprises administering to a mammalian subject in need of body weight reduction an effective amount of dihydroquercetins and root-derived aralosides A, B, C, and D.

6. A method for reducing body fat mass in a mammalian subject in need thereof, which comprises administering an effective amount of dihydroquercetins and root-derived aralosides A, B, C, and D.

* * * * *